United States Patent
Klucker et al.

(10) Patent No.: US 9,504,659 B2
(45) Date of Patent: *Nov. 29, 2016

(54) THERMOREVERSIBLE OIL-IN-WATER EMULSION

(75) Inventors: Marie-Françoise Klucker, Caluire et Cuire (FR); Jean Haensler, Pollionnay (FR); Patricia Probeck-Quelleec, Lyons (FR); Pascal Chaux, Bully (FR)

(73) Assignee: Sanofi Pasteur SA, Lyons (FR)

( * ) Notice: Subject to any disclaimer, the term of this patent is extended or adjusted under 35 U.S.C. 154(b) by 1575 days.

This patent is subject to a terminal disclaimer.

(21) Appl. No.: 11/621,860

(22) Filed: Jan. 10, 2007

(65) Prior Publication Data

US 2007/0191314 A1    Aug. 16, 2007

Related U.S. Application Data

(60) Provisional application No. 60/780,159, filed on Mar. 8, 2006.

(30) Foreign Application Priority Data

Jan. 13, 2006  (FR) ..................... 06 00309

(51) Int. Cl.

| | | |
|---|---|---|
| A61K 31/66 | (2006.01) |
| A61K 9/107 | (2006.01) |
| A61K 31/00 | (2006.01) |
| A61K 31/047 | (2006.01) |
| A61K 39/145 | (2006.01) |
| A61K 45/06 | (2006.01) |
| A61K 39/39 | (2006.01) |
| A61K 39/12 | (2006.01) |
| A61K 39/00 | (2006.01) |

(52) U.S. Cl.
CPC .............. *A61K 31/00* (2013.01); *A61K 9/107* (2013.01); *A61K 31/047* (2013.01); *A61K 31/66* (2013.01); *A61K 39/12* (2013.01); *A61K 39/145* (2013.01); *A61K 39/39* (2013.01); *A61K 45/06* (2013.01); *A61K 2039/55505* (2013.01); *A61K 2039/55511* (2013.01); *A61K 2039/55566* (2013.01); *A61K 2039/70* (2013.01); *C12N 2710/16134* (2013.01); *C12N 2760/16134* (2013.01); *C12N 2760/16234* (2013.01)

(58) Field of Classification Search
CPC .......... C12N 2740/16034; C12N 2760/16234; B82Y 5/00; A61K 9/0019; A61K 39/145; A61K 39/21; A61K 39/39; A61K 9/19; A61K 2039/55566; A61K 47/10; A61K 47/06; A61K 9/1075; A61K 2039/525; A61K 9/107; A61K 31/66; A61K 31/047; A61K 31/00; A61K 47/26
See application file for complete search history.

(56) References Cited

U.S. PATENT DOCUMENTS

| | | | |
|---|---|---|---|
| 5,302,401 A * | 4/1994 | Liversidge et al. | .......... 424/501 |
| 5,547,834 A | 8/1996 | Spaete et al. | |
| 5,718,904 A * | 2/1998 | Hjorth | ........................ 424/278.1 |
| 5,744,062 A * | 4/1998 | Dahms et al. | ................... 516/67 |
| 6,299,884 B1 | 10/2001 | Van Nest et al. | |
| 6,544,518 B1 | 4/2003 | Friede et al. | |
| 6,787,523 B1 | 9/2004 | Schenk | |
| 7,371,395 B2 | 5/2008 | Parisot et al. | |
| 2002/0102562 A1 | 8/2002 | Spaete et al. | |
| 2003/0022852 A1 | 1/2003 | Van Nest et al. | |
| 2003/0153532 A1 | 8/2003 | Hawkins et al. | |
| 2003/0181602 A1 * | 9/2003 | Ansmann et al. | ............. 525/418 |
| 2004/0202669 A1 | 10/2004 | O'Hagan | |
| 2005/0079185 A1 * | 4/2005 | Parisot et al. | ............. 424/184.1 |
| 2005/0164988 A1 | 7/2005 | Hawkins et al. | |
| 2006/0233831 A1 | 10/2006 | Parisot et al. | |
| 2007/0014805 A1 | 1/2007 | Dalencon et al. | |
| 2007/0270507 A1 | 11/2007 | Weiss et al. | |
| 2007/0292418 A1 * | 12/2007 | Fields et al. | ............... 424/133.1 |

FOREIGN PATENT DOCUMENTS

| | | |
|---|---|---|
| CA | 2628424 | 5/2007 |
| WO | WO 2004060396 A2 | 12/2003 |
| WO | WO 2004/060396 * | 7/2004 |
| WO | WO 2005009462 A2 | 7/2004 |
| WO | WO 2006113373 A2 | 4/2006 |
| WO | WO 2007052155 A2 | 11/2006 |

* cited by examiner

*Primary Examiner* — Kortney L Klinkel
*Assistant Examiner* — Lisbeth C Robinson
(74) *Attorney, Agent, or Firm* — McDonnell Boehnen Hulbert & Berghoff LLP

(57) ABSTRACT

The invention relates to a thermoreversible oil-in-water emulsion comprising:
a TLR4 agonist, the chemical structure of which does not comprise a sugar ring,
squalene,
a nonionic surfactant belonging to the polyoxyethylene alkyl ether chemical group,
a hydrophilic surfactant,
an aqueous solvent, and
which shows immunostimulating properties.

3 Claims, No Drawings

THERMOREVERSIBLE OIL-IN-WATER EMULSION

This application claims the benefit of priority of U.S. provisional application 60/780,159, file Mar. 8, 2006.

BACKGROUND OF THE INVENTION

1. Field of the Invention

The invention relates to an immunostimulating composition in the form of a thermoreversible oil-in-water (O/W) emulsion comprising a TLR4 agonist, called TLA4.

TLR4 (toll-like receptor type 4) is a receptor expressed by antigen-presenting cells of the immune system; it is involved in early defense mechanisms against gram-bacterial infections. The lipopolysaccharide (LPS) of gram-bacteria is the natural ligand for TLR4; it activates the receptor, which triggers a cascade of biochemical events, in particular the activation of Nf-Kappa B transcription factor, and the production of pro-inflammatory cytokines. Monophosphoryl lipid A, which comes from the hydrolysis of LPS, is also a ligand for TLR4, with the advantage that it is less toxic than LPS.

2. Summary of the Related Art

WO 2004/060396 describes formulations in the form of O/W emulsions containing a phospholipid adjuvant. The emulsions, which have a submicronic size, are obtained by means of a high pressure homogenizer (microfluidizer). The method of production uses high mechanical energies in order to obtain sufficiently great shear forces to reduce the size of the oil drops. According to this teaching, the emulsion obtained contains drops whose size is approximately 500 nm.

It is desirable to be able to have an alternative formulation to that proposed in that patent application, and especially one which can be obtained by a simpler method (not requiring specific shear technology), involving low energy while at the same time being reproducible, reliable and usable on a large scale; furthermore, the adjuvant formulation must be able to improve the effectiveness of vaccines, by increasing the immune response to an antigen, while at the same time not exhibiting any sign of toxicity which would be detrimental to the completely safe administration thereof.

SUMMARY OF THE INVENTION

To this effect, a subject of the invention is:
An O/W emulsion comprising:
i) a TLR4 agonist, called TLA4, the chemical structure of which does not comprise a sugar ring,
ii) squalene,
iii) an aqueous solvent,
iv) a nonionic hydrophilic surfactant which is a polyoxyethylene alkyl ether,
v) a nonionic hydrophobic surfactant, and which is thermoreversible.

DETAILED DESCRIPTION OF THE INVENTION

The TLR4 agonist contained in the emulsion, according to the invention, is not lipid A or a derivative of lipid A or a molecule which mimics the structure of lipid A. Typically, TLA4 is a chemical compound of formula I, II, III, or IV:

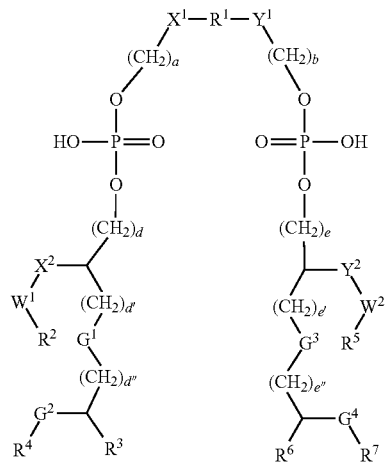

Compound of formula I

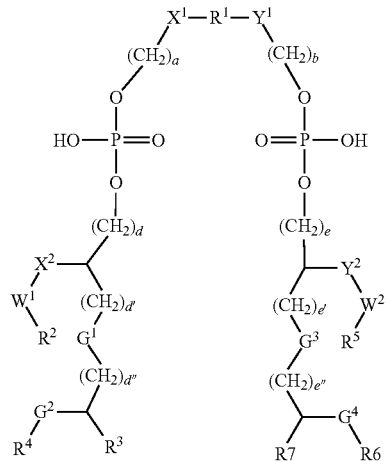

Compound of formula II

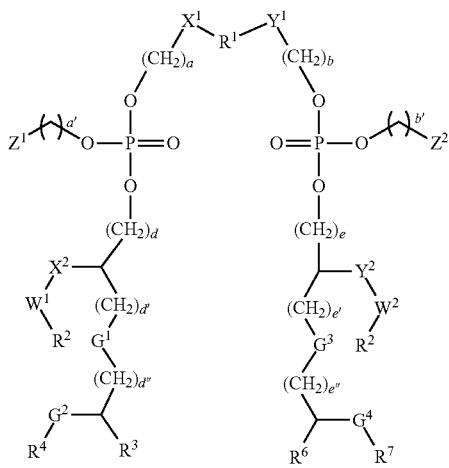

Compound of formula III

-continued

Compound of formula IV

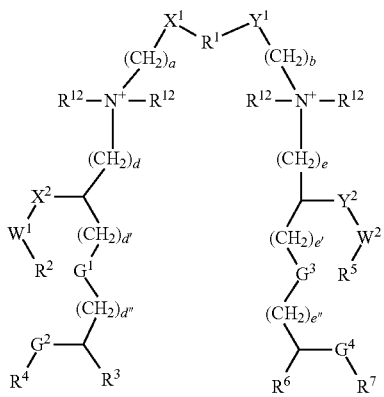

in which, for each of the formulae I, II, III or IV, $R^1$ is selected from the group consisting of:
a) C(O);
b) C(O)—($C_1$-$C_{14}$ alkyl)-C(O), in which said $C_1$-$C_{14}$ alkyl is optionally substituted with a hydroxy, a $C_1$-$C_5$ alkoxy, a $C_1$-$C_5$ alkylenedioxy, a $C_1$-$C_5$ alkylamino or a $C_1$-$C_5$ alkyl-aryl, in which said aryl moiety of said $C_1$-$C_5$ alkyl-aryl is optionally substituted with a $C_1$-$C_5$ alkoxy, a $C_1$-$C_5$ alkylamino, a $C_1$-$C_5$ alkoxy-amino, a $C_1$-$C_5$ alkylamino-$C_1$-$C_5$ alkoxy, —O—$C_1$-$C_5$ alkylamino-$C_1$-$C_5$ alkoxy, —O—$C_1$-$C_5$ alkyl-amino-C(O)—$C_1$-$C_5$ alkyl-C(O)OH, or —O—$C_1$-$C_5$ alkylamino-C(O)—$C_1$-$C_5$ alkyl-C(O)—$C_1$-$C_5$ alkyl;
c) an alkyl comprising a $C_2$-$C_{15}$ straight or branched chain, optionally substituted with a hydroxyl or an alkoxy; and
d) —C(O)—$C_6$-$C_{12}$ arylene-C(O)— in which said arylene is optionally substituted with a hydroxy, a halogen, a nitro or an amino;
a and b are independently 0, 1, 2, 3 or 4;
d, d', d", e, e' and e" are independently an integer from 0 to 4;
$X^1$, $X^2$, $Y^1$ and $Y^2$ are independently selected from the group consisting of a chemical bond, an oxygen, NH and N(C(O) $C_1$-$C_4$ alkyl), and N($C_1$-$C_4$ alkyl);
$W^1$ and $W^2$ are independently selected from the group consisting of carbonyl, methylene, sulfone and sulfoxide;
$R^2$ and $R^1$ are independently selected from the group consisting of:
a) $C_2$ to $C_{20}$ straight chain or branched chain alkyl, which is optionally substituted with an oxo, a hydroxy or an alkoxy;
b) $C_2$ to $C_{20}$ straight chain or branched chain alkenyl or dienyl, which is optionally substituted with an oxo, a hydroxy or an alkoxy;
c) $C_2$ to $C_{20}$ straight chain or branched chain alkoxy, which is optionally substituted with an oxo, a hydroxy or an alkoxy;
d) —NH—$C_2$ to $C_{20}$ straight chain or branched chain alkyl, in which said alkyl group is optionally substituted with an oxo, a hydroxy or an alkoxy; and
e)

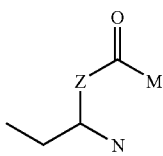

in which Z is selected from the group consisting of O and NH, and M and N are independently selected from the group consisting of $C_2$ to $C_{20}$ straight chain or branched chain alkyl, alkenyl, alkoxy, acyloxy, alkylamino and acylamino;
$R^3$ and $R^6$ are independently selected from the group consisting of $C_2$ to $C_{20}$ straight chain of branched chain alkyl or alkenyl, optionally substituted with an oxo or a fluoro;
$R^4$ and $R^7$ are independently selected from the group consisting of C(O)—$C_2$ to $C_{20}$ straight chain or branched chain alkyl or alkenyl; $C_2$ to $C_{20}$ straight chain or branched alkyl; $C_2$ to $C_{20}$ straight chain or branched chain alkoxy; $C_2$ to $C_{20}$ straight chain or branched chain alkenyl; in which said alkyl, alkenyl or alkoxy groups can be independently and optionally substituted with a hydroxy, a fluoro or a $C_1$-$C_5$ alkoxy;
$G^1$, $G^2$, $G^3$ and $G^4$ are independently selected from the group consisting of oxygen, methylene, amino, thiol, —C(O)NH—, —NHC(O)—, and —N(C(O) $C_1$-$C_4$ alkyl)-;
or $G^2R^4$ or $G^4R^7$ can together be a hydrogen atom or a hydroxy; and in which, for formula III:
a' and b' are independently 2, 3, 4, 5, 6, 7 or 8, preferably 2;
$Z^1$ is selected from the group consisting of —OP(O)(OH)$_2$, —P(O)(OH)$_2$, —OP(O)(OR$^8$)(OH) where
$R^8$ is a $C_1$-$C_4$ alkyl chain, —OS(O)$_2$OH, —S(O)$_2$OH, —CO$_2$H, —OB(OH)$_2$, —OH, —CH$_3$, —NH$_2$ and —N(R$^9$)$_2$ where each $R^9$ is independently a $C_1$-$C_4$ alkyl chain;
$Z^2$ is —OP(O)(OH)$_2$, —P(O)(OH)$_2$, —OP(O)(OR$^{10}$)(OH) where $R^{10}$ is a $C_1$-$C_4$ alkyl chain, —OS(O)$_2$OH, —S(O)$_2$OH, —CO$_2$H, —OB(OH)$_2$, —OH, —CH$_3$, —NH$_2$ or —N(R$^{11}$)$_2$ where each $R^{11}$ is independently a $C_1$-$C_4$ alkyl chain;
and in which, for formula IV:
$R^{12}$ is H or a $C_1$-$C_4$ alkyl chain;
or a pharmaceutically acceptable salt of the compound of formula I, II, III, or IV.

As used herein, the term "dienyl" means an alkyl moiety with two double bonds.

The emulsion according to the invention is thermoreversible, which means that it changes from the state of an O/W emulsion to the state of a W/O emulsion when it is heated to a temperature at least equal to a "phase inversion temperature". On the microscopic scale, the phase inversion temperature reflects the change from a curvature directed toward the oily phase to a curvature directed toward the aqueous phase, this transition necessarily involving the passing through a zero mean curvature phase (the system then being related either to a lamellar phase or to a microemulsion).

According to the invention, such emulsion can be obtained by means of a temperature-variation phase-inversion process, which provides a very large advantage from an industrial point of view because it is easily checked and it is suitable for large scale production. Such a process provides all the guarantees of safety and of profitability necessary for the pharmaceutical industry. In addition, by virtue of this process, it is possible to obtain a monodisperse emulsion, the droplet size of which is very small, which renders the emulsion thus obtained particularly stable and readily filterable by means of sterilizing filters, the cutoff threshold of which is 200 nm.

Advantageously, at least 90% of the population by volume of the oil droplets of the emulsion according to the invention has a size ≤200 nm. In general, at least 50% of the population by volume of the oil droplets of these emulsions has a size ≤110 nm. According to one specific characteristic, at least 90% of the population by volume of the oil droplets has a size ≤180 nm and at least 50% of the population by volume of the oil droplets has a size ≤110 nm.

In general, the thermoreversible emulsion according to the invention is homogeneous. The term "homogeneous emulsion" is intended to mean an emulsion for which the graphic representation of size distribution ("granulogram") of the oil droplets is unimodal. Typically, this graphic representation is of the "Gaussian" type.

Thermoreversible emulsions in which at least 90% of the population by volume of the oil droplets has a size ≤200 nm are particularly preferred from an industrial point of view because they are very stable and can be readily sterilized by means of 0.2 μm filters.

The size of the droplets can be measured by various means, and in particular using laser diffraction particle size analyzers such as the Beckman Coulter devices of the LS range (in particular the LS230) or Malvern devices of the Mastersizer range (in particular Mastersizer 2000). The principle of measurement of these devices is based on analyzing the intensity of the light scattered by the particles as a function of the angle (large, medium and small angle detectors) when the sample is illuminated by a laser beam. This analysis is carried out by means of mathematical models chosen according to the size and the nature of the material used. In the case of the measurement of the size of submicronic particles, it is necessary to apply a specific optical model (Mie theory) taking into account the refractive indices of the oily phase (in this case, 1.495 for squalene) and of the aqueous phase (for example, it is 1.332 for water); it is also necessary to be able to detect the weak intensities emitted by the very fine particles, which requires an additional detection cell for the large-angle polarized intensity differential scattering measurement (PIDS system from Coulter, which allows measurement from 40 nm). The measurements can slightly vary according to the device used and/or the data processing software used.

The phase inversion temperature of a thermoreversible emulsion according to the invention is a characteristic specific to each emulsion and varies according to the nature of its components and to their relative concentrations. Advantageously, the composition of the emulsion according to the invention is chosen such that the phase inversion occurs at a temperature of between 45° C. and 80° C. preferably of between 50 and 65° C. This temperature range is advantageous because there is no risk of the emulsion changing state if it is stored at a relatively high temperature (~37° C.). Furthermore, as in the method for preparing the thermoreversible emulsion, the heating of the components does not exceed 80° C., which contributes to maintaining the structure and integrity of the components and in particular of the TLA4. When the phase inversion temperature of the emulsion is high, in particular when it is greater than or close to 80° C., it may be useful to lower it by adding to the composition of the emulsion an alditol, which is usually chosen from sorbitol, mannitol, glycerol, xylitol or erythritol. When the alditol is used in a concentration range of from 0.1 to 10% (w/w), typically in a concentration range of from 1 to 10% (w/w), and more typically in a concentration range of from 2 to 7% (w/w), the phase inversion temperature of the emulsion can be decreased by approximately 10° C. The phase inversion temperature of the emulsion can also be decreased by replacing the aqueous phase consisting only of water with a buffered saline aqueous phase. A TRIS buffer, a phosphate buffer such as PBS or the Dulbecco PBS buffer without $Ca^{2+}$ or $Mg^{2+}$, or a citrate buffer is normally used.

The chemical compounds of formula I, II, III, or IV are obtained by synthesis according to the processes described in US 2003/0153532 or in US 2005/0164988.

In particular, the TLA4 according to the invention is a chemical compound of formula I,

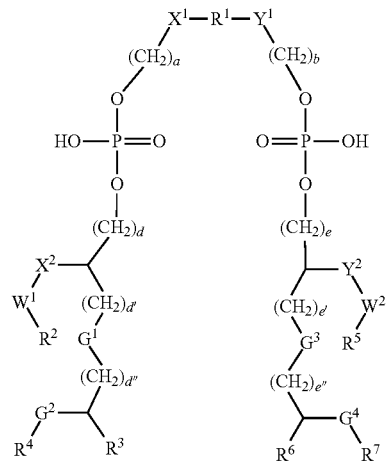

or a pharmaceutically acceptable salt of this compound. Preferably, $R^1$ is C(O) or C(O)—(CH$_2$)$_n$—C(O), n being 1, 2, 3 or 4,
a, b, d, d', d'', e, e' and e'' are independently 1 or 2,
$X^1$, $X^2$, $Y^1$ and $Y^2$ are NH,
$W^1$ and $W^2$ are C(O),
$R^2$ and $R^5$ are selected from the group consisting of $C_{10}$ to $C_{15}$ straight chain alkyl optionally substituted with oxo, NH—$C_{10}$ to $C_{15}$ straight chain alkyl, and

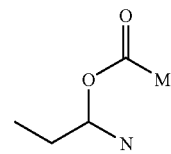

in which M and N are independently a $C_2$ to $C_{20}$ straight chain alkyl or alkenyl,
$R^3$ and $R^6$ are $C^5$ to $C^{10}$ straight chain alkyl,
$R^4$ and $R^7$ are selected from the group consisting of hydrogen, C(O)—$C_8$ to $C_{12}$ straight chain alkyl and C(O)—$C_8$ to $C_{12}$ straight chain alkenyl,
$G^1$ and $G^3$ are an oxygen or —NH(CO)—,
$G^2$ and $G^4$ are an oxygen.

TLA4 exerts an immunostimulating activity in vitro and/or in vivo. The in vitro immunostimulating activity is evaluated in particular:

1) by measuring the increase of TNFα production by the cells of whole human blood, or
2) by measuring the increase of alkaline phosphatase production by a THP-1 line transfected with the alkaline phosphatase gene under the control of the TNFα promoter, or
3) by measuring the increase of cytokine production such as IL-10 and interferon γ by murine splenocytes, or
4) by measuring the increase of TNFα production by the murine macrophage line RAW264, or
5) by measuring the increase of IL-6 production by the U373 human astrocytoma, or 6) by measuring the increase of activation/maturation of dendritic cells derived from human monocytes, on the basis of the expression of activation markets such as CD25, CD80/CD83, by flow cytometry.

All these measurement assays are well known to those skilled in the art and are in particular described in example 7 of US 2003/0153532 or in the Journal of Biological Chemistry, (2001), vol 276/3, page 1873-1880.

The in vivo immunostimulating activity is reflected by an increase in the humoral response and/or in the specific cell response. To evaluate the humoral response, the production of antibodies specific for an antigen is measured. By way of example, reference may be made to the assays which are described in example 8 of US 2003/0153532 for evaluating this response. When the production of specific antibodies (within the form of total immunoglobulins or of a specific isotype) observed following the injection of a TLA4-related antigen is greater than that which is observed subsequent to the administration of the same amount of antigen alone, TLA4 is considered to exert an in vivo immunostimulating activity. The immunostimulating activity of TLA4 can also be evaluated using assays for measuring the specific cellular response, which are well known to those skilled in the art, for instance by measuring the activity of cytotoxic T lymphocytes (CTLs) or lymphoproliferation.

Preferably, TLA4 is chosen from the group consisting of the chemical compounds identified and exemplified in US 2003/0153532 under the names ER803022, ER803058, ER803732, ER803789, ER804053, ER804057, ER804058, ER804059, ER804442, ER804764, ER111232, ER112022, ER112048, ER 112065, ER112066, ER113651, ER118989, ER119327 and ER119328.

The compounds can be in the form of diastereoisomers or in a racemic form (mixture of diastereoisomers) when the chemical structure comprises several asymmetrical carbons. For example, ER804057 and ER804053, which have 4 asymmetrical carbons, are diasteroisomers of ER112066, which is the racemic form. ER804057 is in an (R,R,R,R)-type isomeric configuration, whereas ER804053 is in an (R,S,S,R)-type configuration. Similarly, ER804058, which is in an (R,R,R,R)-type isomeric configuration, and ER804059, which is in an (R,S,S,R)-type isomeric configuration, are diasteroisomers of ER113651, which is the racemic form. ER803022, which is in an (R,R,R,R)-type configuration, ER803732, which is in an (R,S,S,R) configuration, and ER803789, which is in an (R,S,R) configuration, are also diasteroisomers of one and the same chemical molecule. The diasteroisomers which have an R,R,R,R-type configuration, which are generally more active than the other forms, are preferably used. Among these, ER804057 is particularly preferred. It is dodecanoic acid (1R,6R,22R,27R)-1,27-diheptyl-9,19-dihydroxy-9,19-dioxido-14-oxo-6,22-bis[(1,3-dioxotetradecyl)amino]-4,8,10,18,20,24-hexaoxa-13,15-diaza-9,19-diphosphaheptacosane-1,27-diyl ester; it is in the form of a free acid or in the form of a salt. The molecular weight of the free acid form is 1579, that of the disodium salt is 1624. The empirical formula of the disodium salt is $C_{83}H_{158}N_4Na_2O_{19}P_2$.

From a structural point of view, the TLR4 agonist according to the subject of the invention is an amphiphilic molecule. Amphiphilic molecules have a behavior that is both hydrophilic and hydrophobic and have a tendency to precipitate over time. They often dissolve incompletely in organic or aqueous solvents and are often the cause of unstable solutions or solutions that are difficult to reproduce. There exists a need to improve the formulation of these molecules. The emulsion as described in the invention satisfies this need by providing emulsions which are stable over time. An emulsion according to the invention which is stored for 6 months at +4° C. conserves the characteristics that it initially had: the size distribution of the oil droplets does not substantially vary; the milky, fluid and homogeneous aspect of the invention is conserved; and, manifestly, the structural integrity of the TLA4 is not impaired, as shown in example II. It has also been observed that such an emulsion can be stored for at least two days at −2° C. without any significant variation in size distribution of the oil droplets. Moreover, the emulsion as described in the invention is able to decrease the pyrogenic effect of some TLR4 agonists.

The ratio of the amount of TLA4 to the total amount of hydrophilic and hydrophobic surfactants of the emulsion is usually between $0.01 \times 10^{-2}$ and $5 \times 10^{-2}$, more particularly between $0.1 \times 10^{-2}$ and $2 \times 10^{-2}$. In this ratio range, the amount of TLA4 is sufficiently small so as not to exert any influence over the emulsifying capacity of the surfactants, but it is present in sufficient amount to exert an immunostimulating activity in vitro and/or in vivo.

The hydrophilic surfactant according to the invention has an HLB (hydrophilic/lipophilic balance) ≥10 and belongs to the polyoxyethylene alkyl ether (PAE) chemical group, also called polyoxyethylenated fatty alcohol ethers. These nonionic surfactants are obtained by chemical condensation between a fatty alcohol and ethylene oxide. They have a general chemical formula of the type R—(O—CH$_2$—CH$_2$)$_n$—OH in which the radical R usually denotes a saturated or unsaturated alkyl residue and n denotes the number of ethylene oxide units. According to the subject of the invention, R contains between 1 and 50 carbon atoms, preferably between 4 and 20 carbon atoms, and particularly preferably between 10 and 20 carbon atoms n is ≥2 generally between 4 and 50. The emulsion according to the invention usually comprises a single hydrophilic PAE. A mixture of several PAEs is also suitable provided that the overall HLB is ≥10.

The polyoxyethylenated fatty alcohol ethers that are suitable for the subject of the invention can be in a form that is liquid or solid at ambient temperature. Among the solid compounds, preference is given to those which dissolve directly in the aqueous phase or which do not require substantial heating.

Insofar as the number of ethylene oxide units is sufficient, the polyoxyethylenated ethers of lauryl alcohol, myristyl alcohol, cetyl alcohol, oleyl alcohol and/or stearyl alcohol are particularly suitable for the subject of the invention. They have often been given the trade name Brij®, Eumulgin® Simulsol®.

A particularly preferred emulsion according to the invention contains, as nononic hydrophilic surfactant, a polyoxyethylene alkyl ether chosen from the group consisting of ceteareth-12 (sold under the name Eumulgin®B1), ceteareth-20 (Eumulgin®B2), steareth-21 (Eumulgin®S21), ceteth-20 (Simulsol®58), ceteth-10 (Brij®56), ceteth-20 (Brij®58), steareth-10 (Brij®76), steareth-20 (Brij®78), oleth-10 (Brij®96 or Brij®97), and oleth-20 (Brij®98 or Brij®99). The number attached to each chemical name corresponds to the number of ethylene oxide units in the chemical formula.

A compound which is particularly suitable and preferred because of its semi-synthetic origin is Eumulgin®B1 (ceteareth-12) provided by the company COGNIS.

The emulsion according to the invention also contains a nonionic hydrophobic surfactant, the HLB of which is ≤6.

The emulsion usually comprises a nonionic hydrophobic surfactant. A mixture of several nonionic hydrophobic surfactants is also suitable provided the overall HLB is ≤6. Typically, it involves a hydrophobic sorbitan ester or a hydrophobic mannide ester. Sorbitan esters are usually obtained by chemical reaction between a fatty acid and sorbitol, sorbitol monoanhydride or sorbitol dianhydride. Mannide esters are usually obtained by chemical reaction between a fatty acid and mannitol monoanhydride or mannitol dianhydride. Preferably, it involves mannide monooleate (sold by the company Sigma or provided by the company Seppic under the tradename Montanide 80™) or sorbitan monooleate, sold under the name Span®80, provided by the company Cognis under the tradename Dehymuls SMO™ or by the company Seppic under the tradename Montane 80™.

By virtue of the selection of these specific surfactants among all the proposed surfactants in the prior art for preparing emulsions, it has now been found that an O/W adjuvant emulsion can very advantageously be produced by using a phase inversion temperature process.

When the respective concentrations of hydrophilic and hydrophobic surfactants are such that the HLB of the mixture ($HLB_m$ is between 8.5 and 10, and more particularly between 8.6 and 9.6, the emulsions according to the invention are generally homogeneous and often at least 90% of the population by volume of the oil droplets has a size ≤0.2 μm. These emulsions are, moreover, particularly stable. The amounts of hydrophilic and hydrophobic surfactants in the squalene emulsion are preferably adjusted such that the $HLB_m$ is between 8.5 and 10, and more particularly such that the $HLB_m$ is between 8.6 and 9.6. To determine the respective concentrations of hydrophilic and hydrophobic surfactants in the composition of the emulsion, the following formula is used:

$$HLB_m = HLB_e \times M + HLB_{pae} \times (1-M)/100$$

in which, $HLB_m$ corresponds to the HLB of the mixture, which is preferably between 8.5 and 10, and more particularly between 8.6 and 9.6.

$HLB_e$ corresponds to the HLB of the hydrophobic surfactant.

M corresponds to the percentage in weight of the hydrophobic surfactant in the mixture comprising the hydrophobic surfactant and the PAE.

$HLB_{pae}$ corresponds to the HLB of the PAE.

Squalene, which represents the oily phase of the emulsion, has the empirical chemical formula $C_{30}H_{50}$ and comprises 6 double bonds. This oil is metabolizable and has the required qualities to be used in an injectable pharmaceutical product. It comes from shark liver (animal origin) but can also be extracted from olive oil (plant origin). Good results have in particular been obtained using the squalene provided by the company Fluka, which is of animal origin. Generally, the amount of squalene represents between 5 and 45% of the total weight of the emulsion.

The ratio by mass of the amount of squalene to the total amount of surfactants in the emulsion according to the invention is usually between 2.0 and 4.0, preferably between 2.5 and 3.5.

A composition of the emulsion according to the invention that is particularly preferred comprises:
  squalene,
  a phosphate buffer or a citrate buffer as aqueous solvent,
  the compound ER 804057 as TLR4 agonist,
  ceteareth-12 as hydrophilic surfactant,
  sorbitan monooleate as hydrophobic surfactant.

The amount of squalene represents between 5 and 45% of the total weight of the emulsion. The amount of the compound ER804057 usually represents between 0.05% and 2% of the weight of the two surfactants. Preferably, the amounts of ceteareth-12 and of sorbitan monooleate are such that the HLB of the mixture of the two surfactants is between 8.5 and 10, and more particularly between 8.6 and 9.6. The ratio of the amount of squalene to the total amount of ceteareth-12 and of sorbitan monooleate is between 2.0 and 4.0, preferably between 2.5 and 3.5. Furthermore, this composition can contain mannitol, the amount of which is between 0.1% and 10% of the total weight of the emulsion.

The aqueous phase of the emulsion according to the invention can also contain a lyophilization substrate containing one or more cryoprotective agents. The cryoprotective agents are usually chosen from sugars such as sucrose, polyalcohols such as mannitol or sorbitol, or sugar derivatives such as alkylpolyglycosides, for instance sodium decyl-D-galactoside uronate or dodecyl β-maltoside. A lyophilization substrate which contains sucrose, mannitol and dodecyl β-maltoside as a mixture is normally used. The emulsion according to the invention can then be lyophilized and conserved in the form of a lyophilizate. It conserves, however, all its characteristics since, once it is taken up in an aqueous phase, it again becomes a milky, stable and fluid thermoreversible O/W emulsion with an oil droplet size distribution similar to that which preexisted before lyophilization.

The emulsion according to the invention also plays the role of adjuvant of the immune response to an antigen. For the purpose of the present invention, the term "antigen" is intended to mean any antigen which can be used in a vaccine, whether it is a living, attenuated or killed whole microorganism, an extract of a microorganism or a subunit form. When it is in a subunit form, the nature of the antigen is of little importances it may be a peptide, a protein, a glycoprotein, a polysaccharide, a glycolipid, a lipopeptide or a nucleic acid. Among the antigens that are suitable for the subject of the invention, mention is made of the bacterial antigens originating from *Clostridium tetani*, from *Clostridium diphtheriae*, from *Bordetella pertussis*, from *Haemophilus influenzae* type b, from *Streptococcus pneumoniae*, from *Neisseria meningitidis*, from *Shigella* sp, from *Salmonella typhi*, from *Staphylococcus aureus* or *Staphylococcus epidermidis*, from *Mycobacterium tuberculosis*, from *Chlamydia aureus* or from *Streptococcus* sp, viral antigens originating from the hepatitis A, B or C virus, from the flu virus, from the respiratory syncytial virus, from the West Nile virus, from the rabies virus, from the poliovirus, from the HIV virus, from the dengue virus, from the Japanese encephalitis virus, from the yellow fever virus, from the cytomegalovirus or from the herpes virus, from parasitic antigens originating in particular from *Plasmodium* sp. or from tumor antigens. These antigens can be obtained using genetic recombination methods or using extraction methods well known to those skilled in the art. The emulsion according to the invention acts on humoral immunity by increasing the production of specific antibodies and/or on specific cellular immunity by promoting in particular T lymphocyte proliferation, the development of a specific cytolytic T cell response (CTL response) and/or the production of cytokines, chemokines and growth factors, produced by the activated lymphocytes.

For this reason, a subject of the invention is also the use of an emulsion according to the invention, for preparing a vaccine composition. The vaccine composition obtained proves to be more immunogenic, for example because the composition induces a greater specific immune response, whether it is of humoral type and/or of cellular type, or because a smaller amount of antigen is necessary in order to obtain an immune response of the same intensity and of comparable duration. The vaccine composition obtained from an emulsion according to the invention can be administered by any of the routes normally used or recommended for vaccines: parenterally, intradermally, subcutaneously, intramuscularly or mucosally, and can be in various forms, in particular liquid or lyophilized. It can be administered by means of a syringe or by means of a needle-free injector for intramuscular, subcutaneous or intradermal injection, or by means of a nasal spray.

The vaccine composition is generally in the form of a mixture of the antigen with an emulsion according to the invention. It may also be in the form of an extemporaneous formulation. In this case, the antigen and the emulsion according to the invention are brought into contact just before or at the time of the administration of the vaccine composition. For example, the antigen can be lyophilized and taken up with the emulsion just before administration or, conversely, the emulsion can be in a lyophilized form according to the invention and taken up with a solution of the antigen. The vaccine composition can also be in a specific injection device such as the "bypass" syringe when it is desired not to mix the antigen with the emulsion of the invention.

When the vaccine composition is in the form of a mixture obtained by dilution of an emulsion according to the invention with an antigen solution, it is usually in the form of an O/W emulsion in which the amount of squalene in general represents by weight between 0.5 and 5% of the total weight of the composition. It can also be in the form of a thermoreversible O/W emulsion when the amount of squalene in the vaccine composition reaches or exceeds 5% (w/w). When the vaccine composition is a thermoreversible O/W emulsion, it can in particular be in a form in which at least 90% of the population by volume of the oil droplets has a size ≤0.2 µm.

Surprisingly, the emulsion according to the invention has a greater ability to induce neutralizing antibodies than an O/W emulsion of the prior art obtained by microfluidization, the composition of which contains squalene, polyoxyethylene sorbitan monooleate (Tween®80) and sorbitan trioleate (Span®85) (O/W emulsion of the prior art).

Neutralizing antibodies are functional antibodies directed against an infectious microorganisms, produced by an individual who has been immunized with an antigen related to or derived from this microorganism or who has been in contact with this microorganisms, and which prevents infections of the cells by this microorganism. They play a very important role in the prevention or treatment of infections caused by intracellular microorganisms, in particular viruses and single-cell parasites, in particular *plasmodium* sp. Antigens originating from the "sporozoite" form of *Plasmodium falciparum*, (such as the major surface protein of the sporozoite (circumsporozoite protein), LSA3, or the Pfs 16 antigen), and antigens originating from the "merozoite" form of *Plasmodium falciparum* (such as the MSP1, MSP2, MSP3, EBA-175, Rhop-1, Rhop-2, Rhop-3, RAP-1, RAP-2, RAP-3, Pf155/RESA or AMA-1 antigen) induce neutralizing antibodies. The use of an emulsion according to the invention for preparing a vaccine composition containing one or more antigens derived from *Plasmodium falciparum* sporozoites or merozoites is indicated for amplifying the neutralizing immune response. In particular, an emulsion according to the invention can be used for preparing a vaccine composition comprising as vaccine antigen, LSA3 protein from *Plasmodium falciparum*. The gene encoding LSA3 protein was identified by Gardner et al. (Science (1998), 282, 1126-1132) and is localized on chromosome number 2 of strain 3D7 of *Plasmodium falciparum*. The whole sequence of the gene is 12240 bp long and encodes a 1558 amino acid protein sequence. The nucleotide sequence and the protein sequence can be found under the respective accession numbers AE001424 and uniprot O96275-PLAF7 in the EMBL data bank. As vaccine antigen, one can use the whole protein, or peptides or fragments thereof, as for example, those described in WO02/38176. More usually, the vaccine antigen is the whole protein (which may contain one or several point mutations to take into consideration the variations which exist between the strains of *Plasmodium falciparum*) or a fragment of the whole protein, the amino acid sequence of which has at least 80% identity with the whole amino acid sequence described in O96275-PLAF7. The effectiveness of antiviral vaccines is, in certain cases, correlated with the titer of neutralizing antibodies that they induce. This is the case of the flu vaccine, the effectiveness of which is related to the titer of inhibiting-hemagglutination antibodies (IHA).

The emulsion according to the invention is used to prepare a vaccine composition for the treatment or prevention of infectious diseases in humans or animals (birds, horses) linked to the flu virus. Depending on the nature of the flu vaccine, the vaccine composition can be in various forms:

When the flu vaccine contains one or more inactivated whole or "split" virus strains, or is in the form of a subunit vaccine containing purified hemagglutinin from one or more viral strains, or in the form of virosomes (Berna vaccine), the vaccine composition is usually in the form of a mixture, of an O/W emulsion or of a thermoreversible O/W emulsion.

When the flu vaccine contains one or more live attenuated virus strains, the vaccine composition is preferably in a device, of the bypass syringe type, such that the live virus is not in direct contact with the emulsion. The viral suspension and emulsion according to the invention are in two different compartments of the syringe.

The flu vaccines are manufactured from flu viruses cultivated on eggs or on cells according to methods well known to those skilled in the art, and all comprise, as an essential component, the hemagglutinin of one or more virus strains.

A subject of the invention is therefore also the use of an emulsion according to the invention, for preparing a vaccine composition comprising, as vaccine antigen, hemagglutinin(s) from one or more flu virus strain(s). Such vaccine composition is suitable to vaccinate:

a) influenza virus-seronegative populations; it includes individuals who have never been in contact or sensitized with the flu virus or its immunogenic components, or individuals who have never been in contact with a new pandemic strain of influenza virus; or b) influenza virus-seropositive populations; it includes individuals who have already been in contact or sensitized with the flu virus or its immunogenic components; or c) elderly people who have often an alteration of the cellular or of the humoral immunity against the flu virus.

The emulsion according to the invention is also used to prepare a vaccine composition for the treatment or prevention of infectious diseases caused by herpes virus such as HSV1, HSV2 or cytomegalovirus (CMV). In CMV infections, the antibodies directed against the viral envelope proteins, mainly glycoprotein B (gB) and glycoprotein H (gH), and which neutralize the viral infection, play a very important role in the development of a protective immunity. The use of an emulsion according to the invention in the preparation of a vaccine composition containing a CMV envelope protein has the effect of increasing the production of neutralizing antibodies.

A subject of the invention is therefore the use of an emulsion according to the invention, for preparing a vaccine composition comprising, as vaccine antigen, a CMV envelope antigen. Typically, the antigen is the gB glycoprotein and/or the gH glycoprotein. It may also be a peptide or a polypeptide derived from gB and/or from gH, comprising one or more neutralizing epitopes.

gB in its native form (gp130), encoded by the UL 55 gene of CMV, is a glycoprotein of 906 or 907 amino acids, depending on whether the AD169 strain or the Towne strain is involved. The protein sequences of these two strains are described in US 2002/0102562 (FIG. 2). The native form of gB contains an amino acid signal sequence followed by an extracellular domain containing an endoproteolytic cleavage site between residues arginine 460 and serine 461, by a transmembrane domain and by an intracellular domain. Several antigenic domains inducing neutralizing antibodies have been described. Notably, it includes the domain that is located between amino acid residues 461 and 680 of gp 130, this domain being subdivided into two discontinuous domains, the domain between residues 461 and 619 and the domain between residues 620 and 680 (U.S. Pat. No. 5,547, 834). It also includes the antigenic domain 1 (AD-1) located between amino acid residues 552 and 635, or the antigenic domain 2 (AD-2) located between amino acid residues 50 and 77 (Journal of General Virology (1999, 80, 2183-2191; Journal of Virology (2005), 79, 4066-4079). Consequently, a polypeptide which comprises, in its amino acid sequence, a sequence homologous to one or several of the above cited anigenic domains are suitable for the subject of the invention. Typically, the polypeptide comprises, in its amino acid sequence, a sequence homologous to that which is between residues 461 and 680 of gp 130 or more specifically to that which is between residues 552 and 635. The term "homologous sequence" is intended to mean an amino acid sequence in which there is at least 80% identity with the amino acid sequence of the antigenic domain being considered of gp 130 originating from the Towne or AD169 strain (which are described in US 2002/0102562). Typically, the sequence homology is based on a sequence identity of at least 90% and, even more specifically, the sequence homology is based on a sequence identity of 100%.

Among the gB-derived peptides or polypeptides that are suitable for the subject of the invention, mention is in particular made of gp 55 as described in U.S. Pat. No. 5,547,834. It is derived from the cleavage of gB at the endoproteolytic cleavage site; its amino acid sequence corresponds to that which is between serine residue 461 and the C-terminal end. Truncated forms of gp 55 can also be used, such as a gp 55 depleted of all or part of the transmembrane sequence and of all or part of the intracellular C-terminal domain (for example, a peptide having a sequence homologous to the amino acid sequence of gp130 between residues 461 and 646) or a gp 55 depleted of all or part of the intracellular C-terminal domain (for example, a peptide having a sequence homologous to the amino acid sequence of gp130 between residues 461 and 680) which are described in U.S. Pat. No. 5,547,834. It is also possible to use a mutated form of gB which carries one or more mutations at the endoproteolytic cleavage site such that the latter is made ineffectual. The mutation(s) is (are) located between residues 457 and 460 of the sequence of gp130, and more particularly are located at arginine 460 and/or lysine 459 and/or arginine 457. A CMV envelope antigen that is particularly suitable for the subject of the invention is a truncated form of gB depleted of all or part of the C-terminal domain and/or depleted or all or part of the transmembrane sequence and in which the cleavage site is ineffectual. A truncated form of gB which is particularly preferred corresponds to that which is described in U.S. Pat. No. 6,100,064, called gBdTM; it carries three mutations at the cleavage site and a deletion in the transmembrane region between amino acid residues valine 677 and arginine 752, such that the extracellular domain is directly connected to the cytoplasmic domain.

The gB protein or the peptides or polypeptides derived therefrom are obtained by means of genetic recombination methods and purified according to methods well known to those skilled in the art. The methods described in U.S. Pat. No. 6,100,064 and in US 2002/0102562, incorporated by way of reference, can in particular be used. To increase their immunogenicity, they can secondarily be conjugated to a carrier protein or fused to other proteins, in particular to particle-forming proteins such as the hepatitis B surface antigen (HbS). The gB protein or the peptides derived therefrom can also be expressed by recombinant viruses, in particular by recombinant adenoviruses or recombinant poxviruses. To prepare these recombinant vectors expressing gB or derived peptides, the methods which are described in particular in U.S. Pat. No. 6,162,620, U.S. Pat. No. 5,866, 383, U.S. Pat. No. 5,552,143, U.S. Pat. No. 6,183,750, U.S. Pat. No. 5,338,683 or WO 9215672 or in WO 9639491 are used. gB can also be provided by a strain of CMV which has been attenuated by successive passages on cell cultures, in particular the Towne strain which has already been tested for vaccine purposes.

The gH protein is encoded by the UL 7.5 gene of CMV. It is a glycoprotein of 742 or 743 amino acids depending on whether the strain is the Towne strain or the AD169 strain. The sequences are described in U.S. Pat. No. 5,474,914 (FIG. 1) and in U.S. Pat. No. 6,610,295 (FIG. 5(a)). The protein sequence of gH deduced from its nucleotide sequence contains a signal peptide followed by an extracellular domain that does not have an endoproteolytic cleavage site, by a transmembrane domain and by a C-terminal cytoplasmic domain. The neutralizing epitopes are in the extracellular domain, mainly in the N-terminal portion of this domain, more specifically between amino acid residues 15 and 142 of the protein sequence of native gH, and even more specifically between amino acid residues 33 and 142. A major neutralizing epitope of the AD 169 strain has been identified and is between residues 33 and 43 of the sequence of gH, and has the sequence LDPHAFHLLL (Urban M et al.: J. Virol (1992, vol 66/3, p 1303-1311)). Consequently, a polypeptide which comprises, in its amino acid sequence, a sequence homologous to the sequence LDPHAFHLLL or a sequence homologous to that which is between residues 15 and 142 or between residues 33 and 142 of the protein sequence of gH is suitable for the subject of the invention. The term "homologous sequence" is intended to mean an amino acid sequence which has at least 80% identity with either the amino acid sequence which is between residues 15 and 142 or between residues 33 and 142 of the protein sequence of gH of the AD 169 strain or either with the sequence LDPHAFHLLL. More particularly, the sequence homology is based on a sequence identity of at least 90% and, even more specifically, the sequence homology is based on a 100% sequence identity.

As gH-derived peptides or polypeptides that are suitable for the subject of the invention, mention is made of gH depleted of all or part of its transmembrane region and/or depleted of all or part of its cytoplasmic region. Typically, this corresponds to a gH protein from which at least 5 C-terminal residues, preferably at least 10 C-terminal residues, and even more preferably between 20 and 34 residues of the C-terminal end of the amino acid sequence have been deleted.

The gH protein and the polypeptides or the peptides derived therefrom are obtained by means of genetic recombination methods and purified according to methods well known to those skilled in the art, in particular those described in U.S. Pat. No. 5,474,914 or in U.S. Pat. No. 5,314,800, incorporated by way of reference. To increase their immunogenicity, they can be secondarily conjugated to a carrier protein. They can also be produced in the form of fusion proteins, as described in J. Virol (1992, vol 66/3, p 1303-1311). The gH protein and the polypeptides and the peptides derived therefrom can also be expressed by recombinant viruses, in particular by recombinant adenoviruses or recombinant poxviruses. To prepare these recombinant vectors expressing gH or derived forms, the methods which are described in particular in U.S. Pat. No. 6,162,620, U.S. Pat. No. 5,866,383 or U.S. Pat. No. 5,552,143, or in WO 9639491 are used. The gH protein can also be provided by a strain of CMV which has been attenuated by successive passages on cell cultures, in particular the Towne strain which has already been tested for vaccine purposes.

One can also use as vaccine antigen, a protein which results from the fusion between gB or gH glycoprotein (or a fragment thereof) and a membrane protein of HSV1 or HSV2 (or a fragment thereof). For instance, the fusion proteins described in EP 0759995, and in particular the proteins called, gB 685* and gB685**, which result from the fusion between a portion of the gB glycoprotein and a portion of the gD of HSV are suitable vaccine antigens.

Depending on the nature of the CMV antigen, the vaccine composition can be in various forms:

When the antigen is a protein or a peptide, the vaccine composition can be in the form of a mixture, of an O/W emulsion or of a thermoreversible O/W emulsion. It can also be in the form of an extemporaneous preparation which is prepared just before administration. The vaccine composition can also be inside a device, such as a "bypass" syringe which physically separates the antigen from the emulsion.

When the CMV antigen is in the form of a recombinant virus expressing gB, gH or a peptide derived from gB or gH, or when it is in the form of an attenuated strain of a CMV, the antigen and the emulsion according to the invention are not usually directly in contact in the vaccine composition. The antigen and the emulsion can be inside a device which physically separates them, such as a "bypass" syringe, but they are administered at the same time at the same site of administration.

The emulsion according to the invention directs the CD4+ T cell response towards a Th1 pathway by increasing the level of Th1 cytokine production (IL2, IFNγ, . . . ) and/or by decreasing the level of Th2 cytokine production (IL4, IL5, IL10, . . . ) in response to an antigenic stimulus which is presented in the context of MHC Class II molecules. This effect can be assessed by the IFNγ/IL5 ratio which can be calculated from the IFNγ and IL5 cytokines produced after in vitro restimulation with an antigen, which is related to the one which was used for in vivo immunization. One can also assess indirectly the pathway of the CD4+ T cell response by the specific IgG2a/IgG1 ratio which can be calculated from the specific Ig2a and IgG1 responses obtained after mouse immunization with a vaccine composition according to the invention.

The emulsion according to the invention can also be used to correct disequilibrium of the CD4+ T cell response, which can be observed in individuals who have a deficit or an alteration of the immune system. It includes, among others, elderly people who have a lower IFNγ and/or IL2 production in response to an in vitro stimulation with antigens from intracellular germs, in particular with antigens from flu (Ouyang and al. (Mechanisms of ageing and development), 2000, vol 121, 131-137).

Accordingly, a subject of the invention is the use of an emulsion according to the invention for the manufacture of a vaccine composition intended to individuals who displays a disequilibrium of the of the CD4+ T cell response, in particular to elderly people.

A further subject of the invention is a method for preparing an O/W emulsion according to the invention, comprising a step wherein the inverse W/O emulsion is obtained by heating and a step wherein the W/O emulsion is transformed into a O/W emulsion by decreasing the temperature. The W/O emulsion is transformed into a O/W emulsion when the temperature is below the phase inversion temperature of this emulsion.

According to one embodiment of the method, the inverse W/O emulsion is obtained by mixing in a first step an aqueous phase which comprises an aqueous solvent, a polyoxyethylene alkyl ether and a TLR4 agonist with an oily phase which comprises squalene, and a nonionic hydrophobic surfactant so as to obtained an O/W emulsion and by heating in a second step the O/W emulsion at a temperature which is at least the phase inversion temperature.

The aqueous phase, comprising the aqueous solution (usually a buffered solution), the TLR4 agonist (if it is not in the oily phase) and the nonionic hydrophilic surfactant is incorporated into the oily phase, comprising the squalene, and the nonionic hydrophobic surfactant, or conversely: the oily phase is incorporated, into the aqueous phase. This incorporation is done under mechanical stirring. A non calibrated, unstable coarse O/W emulsion (preemulsion) is obtained. This preemulsion is heated with mechanical stirring until phase inversion is obtained, i.e. a W/O emulsion is obtained. The phase inversion or transition can be followed by conductimetry. The temperature at which the curvature change reflecting the passage from one type of emulsion to another occurs is the phase inversion temperature. In reality, this temperature is a temperature range rather than a very specific point value; in fact, it may be considered that this temperature is capable of varying by one or two degrees, so that the entire emulsion undergoes the phase inversion phenomenon. When the emulsion is in the form of a W/O emulsion, an abrupt drop in the conductivity is observed. The heating is stopped and the mixture is cooled. The cooling can be carried out passively, by simply allowing the temperature to return spontaneously to ambient temperature, or more actively, by, for example, immersing the emulsion in an ice bath. During the decrease in temperature, the W/O emulsion will again inverse at the phase inversion temperature so as to again give an O/W emulsion. The emulsion can be stored as it is while awaiting dilution with a solution comprising the vaccine antigen it is thermoreversible, which means that, if it is again brought to a temperature at least equal to the phase inversion temperature, it will again become a W/O emulsion. The phase inversion temperature is usually between 45 and 80° C., and typically between 50 and 65° C. The components of the emulsion, in particular the TLR4 agonist, are thus subjected to moderate heating which prevents evaporation of the aqueous phase or chemical degradation of the components.

According to another embodiment, the inverse W/O emulsion is obtained by heating separately, at a temperature which is at least the phase inversion temperature of the emulsion, an aqueous phase which comprises an aqueous solvent, a polyoxyethylene alkyl ether and a TLR4 agonist and an oily phase which comprises squalene and a non ionic hydrophobic surfactant and then by mixing the aqueous phase with the oily phase while maintaining the temperature at least at the phase inversion temperature.

Practically. The aqueous and oily phases are heated separately to a temperature slightly above the phase inversion temperature) before mixing them to give a W/O inverse emulsion, which will subsequently be cooled until the submicronic O/W emulsion is obtained. These operations can be carried out in separate containers for a batch preparation.

It is also possible to use an on-line manufacturing method. The method consists in mixing, under hot conditions, the two aqueous and oily phases prepared separately, through a thermostatted static mixer, followed by on-line cooling through a refrigerated heat exchanger connected at the outlet of the static mixer, and then by the final recovery of the emulsion according to the invention in an appropriate container (flask or reactor). A static mixer consisting of a succession of mixing elements composed of crossed blades that are sloping with respect to the axis of the tube into which they are introduced has been successfully used. The energy required for the mixing is provided by the pumps which convey the fluids and the mixing is carried out without moving parts, through the mixing elements by successive separation, displacement and combination of the constituents of the mixture.

The on-line manufacturing method is carried out in the following way: the aqueous phase and the oily phase are prepared separately, as above, in two flasks or reactors. The two phases are heated with stirring to a temperature slightly above the phase inversion temperature. The two phases are then introduced into a thermostatted static mixer by means of 2 pumps, the flow rates of which are regulated so as to obtain the composition of the emulsion according to the invention. The W/O inverse emulsion is obtained during the passage of the two phases through the static mixer. The inverse emulsion is subsequently cooled by on-line passage through a refrigerated heat exchanger connected at the outlet of the static mixer. The W/O emulsion will then inverse through the refrigerated heat exchanger to give rise to an O/W emulsion, which will be collected in a flask or reactor and the characteristics of which are identical to those of the emulsion obtained by means of a batch method.

Alternatives to the embodiments of the method which have just been described exist; when the behavior or the TLR4 agonist is more hydrophobic than hydrophilic, it is introduced into the oily phase rather than into the aqueous phase. The TLR4 agonist can also be introduced once the mixing of the oily phase and the aqueous phase has been carried out, or, even when the emulsion has already been heated and it is in a W/O emulsion form. The aqueous phase can also contain an alditol. Lastly, the method for preparing an emulsion according to the invention may comprise several cycles of thermoinversion.

A subject of the invention is also a method for preparing a vaccine composition, comprising a step in which a vaccine antigen is added to an O/W emulsion comprising a TLR4 agonist, the chemical structure of which does not comprises a sugar ring, characterized in that said O/W emulsion has been obtained by a phase inversion temperature process comprising a step in which the inverse W/O emulsion is obtained by heating and a step in which the W/O emulsion is transformed into a O/W emulsion by decreasing the temperatures.

A simple embodiment consists in mixing an aqueous solution of a vaccine antigen into a thermoreversible O/W emulsion obtained according to one of the embodiments which have just been described. The vaccine composition obtained is in the form of an O/W emulsion or in the form of a thermoreversible O/W emulsion when the amount of squalene represents by weight at least 5% of the total weight of the vaccine composition. Alternatively, the vaccine antigen can be mixed with the aqueous phase or the oily phase before implementing the process of preparing the emulsion according to the invention. Such a process can be implemented only if the antigens are compatible with the thermoinversion process. The aqueous solutions of the antigen can also contain mineral salts, one or more buffers and any compound that is currently used in vaccines, such as stabilizers, preservatives, or even other adjuvants. By way of indication, the antigen concentration in the aqueous solutions is generally between 1 µg/ml and 1 mg/ml.

The method according to the invention can also include a lyophilization step. A concentrated liquid emulsion is first prepared as has just been described, but preferably choosing, as aqueous solution, water rather than a buffered solution. This emulsion is subsequently diluted in a lyophilization substrate comprising an alditol, a sugar and an alklylpolyglycoside. A lyophilization substrate normally used comprises mannitol, sucrose and dodecyl maltoside. The diluted emulsion is then divided up into samples (for example 0.5 ml) and subjected to a lyophilization cycle which can be carried out in the following way:
    loading of the samples at +4° C.,
    freezing for approximately 2 hours at a set temperature of −45° C.,
    primary desiccation for 14 to 19 hours at a set temperature of 0° C.,
    secondary desiccation for 3 hours 30 min at a set temperature of +25° C.

The lyophilizate obtained is generally conserved at a temperature in the region of +4° C. before being mixed with one or, more vaccine antigens. A vaccine composition according to the invention can be thus prepared by taking up the lyophilized emulsion with an aqueous solution of antigens, and can then be conserved as it is (i.e. in the liquid state), or can be subjected to a further lyophilization cycle in order to be conserved in the form of a lyophilizate, if the nature of the antigens allows this. Alternatively, it is possible to directly dilute the concentrated emulsion with an aqueous solution comprising both the vaccine antigens and the alditol, the sugar and the alkylpolyglycoside, and to subsequently subject the composition obtained to lyophilization. Such a manner of carrying out the procedure implies, of course, that the antigens are compatible with a lyophilization process.

The examples which follow illustrate various embodiments of the invention in a nonlimiting manner.

EXAMPLE I

Preparation of a Concentrated Thermoreversible O/W Emulsion Containing 32.4% of Squalene (w/w)

A solution of mannitol at 18% in phosphate buffer (w/w) was prepared with mechanical stirring at 40° C. 0.093 g of Eumulgin™ B1 was added to 0.454 g of this solution, which was homogenized with mechanical stirring at 40° C. for 5 min.

A stock suspension containing 1000 μg/ml of the chemical compound ER804057 in a 50 mM Tris buffer was prepared. 390 μl of the stock suspension of ER804057 was added to the Eumulgin™ B1/mannitol mixture.

In another container, 0.073 g of Dehymuls™ SMO was mixed with 0.484 g of squalene and the mixture was homogenized by mechanical stirring for 5 minutes at 30° C.

The content of the aqueous phase containing ER804057 was subsequently incorporated, with stirring at approximately 30° C., into the oily phase containing the Dehymuls™ SMO/squalene mixture.

The crude emulsion obtained was heated, with mechanical stirring, until the temperature reaches 60° C. This temperature corresponds to the phase inversion temperature of this composition. The emulsion is under the form of inverse W/O emulsion.

The heating was subsequently stopped, but the stirring was maintained until the temperature reaches the ambient temperature of the laboratory (~20° C.). The emulsion becomes again under the form of an O/W emulsion.

A homogeneous thermoreversible O/W emulsion was obtained, in which more than 90% of the population by volume of the oil droplets has a size ≤200 nm and in which the composition by mass percent was as follows:
  32.4% of squalene,
  6.2% of ceteareth-12 (Emulgin B1),
  4.9% of sorbitan monooleate dehymuls SMO),
  5.5% of mannitol
  0.026% of ER804057

The amount of squalene in this adjuvant emulsion therefore represents 32.4% of the total weight of the emulsion.

In another embodiment, a mixture comprising 50.5 g phosphate buffer, 6 g mannitol, 6.18 g Eumulgin™ B1, 0.026 g ER804057 was prepared under mechanical stirring at 40° C. In another container, oily phase was prepared by mixing 32.5 g squalene with 4.8 g Deshymuls™ SMO. When the phases were homogeneous, the incorporation of the aqueous phase in the oily phase, the steps of increase of temperature and of decrease of temperature were performed in the same conditions.

A homogeneous thermoreversible O/W emulsion was obtained as previously, in which more than 90% of the population by volume of the oil droplets has a size ≤200 nm and in which the composition by mass percent was as follows:
  32.5% of squalene,
  6.2% of ceteareth-12 (Emulgin B1),
  4.8% of sorbitan monooleate (dehymuls SMO),
  6% of mannitol
  0.026% of ER804057
  50.5% of phosphate buffer.

In another embodiment, phosphate buffer was replaced by a citrate buffer; pH 6.04 prepared by mixing 0.83 mM citric acid with 9.14 mM citrate Na.

This concentrated squalene emulsion was used as a "stock" emulsion, from which were derived dilute thermoreversible O/W emulsions by dilution in a phosphate buffer, in a Tris buffer, or in a citrate buffed; before being sterilized by filtration (see example II). These dilute O/W emulsions were subsequently mixed with one or more vaccine antigens (see examples III, IV and V).

EXAMPLE II

Study of the Stability of a Dilute Thermoreversible O/W Emulsion Containing 5% of Squalene (w/w)

The concentrated emulsion of example I was diluted in a 9.6 mM phosphate buffer (pH=7.4) so as to obtain a dilute emulsion in which the amount of squalene represented 5% of the total weight of the emulsions. The composition of the dilute emulsion, called PIT-ER804057 at 5%, was as follows:
  Squalene: 50 mg/ml
  Ceteareth-12 (Emulgin B1): 9.5 mg/ml
  Sorbitan monooleate (dehymuls SMO): 7.5 mg/ml
  Mannitol: 9 mg/ml
  ER804057: 40 μg/ml The stability of this thermoreversible emulsion was evaluated after storage for 6 months at a temperature of +4° C. by verifying the ER804057 content in the emulsion and by checking the size distribution of oil droplets in the emulsion. To assay ER804057, a selective extraction of ER804057 from the emulsion was carried out, followed by analysis by high performance liquid chromatography (HPLC) coupled to UV detector equipped with diode hair clips. The ER804057 content of the emulsion to be verified was determined using a standard range containing between 5 and 25 μg/ml of ER804057. In order to compensate for the variations in extraction yields, a constant amount of an internal standard, the chemical structure of which is very similar to that of ER804057, was introduced into each sample to be assayed (including into the samples of the standard range). This internal standard was the chemical molecule called ER803022.

The standard range was prepared from a thermoreversible emulsion which had the same composition and was prepared in the same way as the dilute PIT-ER804057 at 5% emulsion, except that it did not contain any ER804057 (emulsion PIT at 5%), to which were added a varying amount of ER804057 taken from a stock solution of ER804057 at 0.1 mg/ml of a mixture containing 2 volumes of chloroform per volume of methanol (mixture CM 2:1), and a fixed amount of an internal standard (10 μg), taken from a stock solution of an internal standard at 0.1 mg/ml of mixture CM 2:1, which was diluted as appropriate in water for injectable preparation.

The sample of PIT-ER804057 at 5% to be assayed was prepared by taking an aliquot of the emulsion PIT-ER804057 at 5%, to which 10 μg of internal standard was added, and which was diluted in water for injectable preparation.

The extraction of ER804057 from the samples of the standard range or from the samples of PIT-ER804057 at 5% was carried out in the following way: The sample was solubilized with CM2:1. The two-phase system obtained was composed of a chloroform phase containing predominantly ER804057 and an aqueous phase containing the other compounds of the emulsion. The chloroform phase was recovered and evaporated under hot conditions under a stream of nitrogen. The dry extract obtained was taken up and again solubilized in the CM2:1 mixture. The mixture was loaded onto an anion exchange cartridge pre-equilibrated in the CM2:1 mixture. It selectively retains ER804057 and the internal standard which were negatively charged, whereas the other components of the emulsion, which were not charged, were eliminated, ER804057 and the internal standard were eluted by means of a mixture containing 2 volumes of chloroform and 3 volumes of methanol, per volume of 1M NaCl. The eluate was subsequently dried under hot conditions under a stream of nitrogen. Finally, a final extraction was carried out with water and CM2:1 so as to eliminate the residual salts and to recover ER804057 and the internal standard in the chloroform phase, which was finally evaporated under hot conditions under a stream of nitrogen. The dry extract derived from each sample was conserved at −20° C. before being analyzed by HPLC.

The dry extract of each sample was taken up with 50 µl of CM4:1, and then diluted to ½ in methanol, then to ¹/₁₀th in a mixture of 30% acetonitrile-water for injectable preparation, 20 µl of the dilution were injected into a liquid chromatography apparatus (HPLC Merck Hitachi, serie 7000) comprising a Waters XTerra™ RP8 column pre-equilibrated in a mobile phase consisting of a mixture of 80% of phase A (water for injectable preparation/ethanol 50/50 containing 2% $H_3PO_4$) and 20% of phase B (ethanol containing 2% $H_3PO_4$), ER804057 and the internal standard were eluted using a gradient of ethanol containing 2% $H_3PO_4$. At the outlet of the HPLC, the eluate meets the UV detector and the molecules are detected at the wavelength of 215 nm. The surface areas corresponding to the two peaks (analyte and reference) on the chromatogram were integrated and correlated. To correct the variations related to the preparation of the sample, the standard curve was established between the ratio of the surface areas of the peaks corresponding to the ER804057/internal standard couple and the ratio of the concentrations corresponding to the ER804057/internal standard couple. Once the curve was established, the amount of ER804057 present in the emulsion PIT-ER804057 at 5% was then determined by measuring the ratio of the surface areas of the ER804057/internal standard peaks.

|  | 1 month at +4° C. | 3 months at +4° C. | 6 months at +4° C. |
|---|---|---|---|
| ER 804057 (theoretical concentration: 40 µg/ml) | 38 µg/ml | 37 µg/ml | 42 µg/ml |

The results that were obtained show that ER804057 conserves its structural integrity and that its concentration in the emulsion PIT-ER804057 at 5% has not substantially varied after the emulsion has been conserved for 6 months at +4° C.

After ¹/₁₀₀$^{th}$ dilution of the emulsion PIT-ER804057 at 5% the analyses of size distribution were performed with the mastersizer 2000 using the following parameters:

Refractive index (particle)=1.495; Refractive index (medium)=1.332; absorption value=0; lower obscuration limit: 4%; upper obscuration limit, 7%; analytical model: "general purpose".

For each analysis of size distribution, the following parameters were measured: d10, d50 and d90 which represent respectively the values of particle diameters for which, respectively, 10%, 50% and 90% of the population by volume of oil droplets are of a smaller size.

|  | T = 0 | T = 3 months | T = 6 months |
|---|---|---|---|
| d10 | 71* | 71 | 70 |
| d50 | 103 | 100 | 101 |
| d90 | 155 | 152 | 153 |

*in nm

The results that were obtained show that the size distribution of the PIT-ER804057 at 5% is stable at +4° C. for at least 6 months.

EXAMPLE III

Vaccine Composition Against Cytomegalovirus Infections, Prepared from an O/W Emulsion According to the Invention Vaccine compositions comprising, as vaccine antigen, a recombinant protein which derives from the gB glycoprotein of CMV were prepared. This recombinant protein was produced by a recombinant CHO line transfected with a plasmid called pPRgB27clv4, which contains a modified gB gene. To facilitate the production of this recombinant protein by the CHO line, the gB gene, the sequence of which is described in U.S. Pat. No. 5,834,307, was modified beforehand by deleting the part of the gene which encodes the transmembrane region of the gB protein corresponding to the amino acid sequence between valine 677 and arginine 752 and introducing 3 point mutations at the cleavage site. The protein produced by the CHO line, called gBdTM, corresponds to a truncated gB protein depleted of the cleavage site and of the transmembrane region.

The construction of the plasmid pPRgB27clv4 and the production of the truncated gB protein (gBdTM) by the recombinant CHO line are described in U.S. Pat. No. 6,100,064. The gBdTM protein produced in the culture medium was subsequently purified by affinity chromatography using the monoclonal antibody 15D8 described by Rasmussen L et al. (J. Virol. (1985) 55: 274-280). The purified protein was purified in the form of a stock solution containing 0.975 mg/ml of gBdTM in phosphate buffer.

Immunostimulating compositions of gBdTM formulated with various compositions of O/W emulsions or with a suspension of aluminum hydroxide were prepared.

Composition No. 1 contained 2 µg of gBdTM in citrate buffer at pH 6 in 50 µl (group gB).

Composition No. 2 contained 2 µg of gBdTM, 1.075 mg of squalene, 0.133 mg of sorbitan trioleate (Montane™ VG 85) and 0.125 mg of Tween™80 in citrate buffer at pH 6 in 50 µl (group gB+O/W emulsion). This composition was obtained by mixing, volume for volume, a solution of gB with an O/W emulsion of the prior art which was obtained by microfluidization.

Composition No. 3 contained 2 µg of gBdTM and 60 µg of aluminum hydroxide in phosphate buffer in 50 µl (group gB+AL).

Composition No. 4 contained 2 µg of gB, 1.25 mg of squalene, 0.187 mg of Dehymuls™ SMO, 0.237 mg of Eumulgin™ B1 and 0.225 mg of mannitol in PBS buffer at pH 7.4 in 50 µl. This composition was obtained by mixing, volume for volume, a solution of gB with a thermoreversible O/W emulsion containing 5% of squalene (group gB+PIT). The thermoreversible O/W emulsion used to prepare this composition was obtained by dilution of a concentrated thermoreversible O/W emulsion containing 32.5% of squalene (w/w), which was prepared using the same method as that described in example 1, except for the fact that the aqueous phase did not contain any ER804057.

Composition No. 5 contained 2 µg of gBdTM and 1 µg of ER804057, in a citrate buffer, pH 6, in 50 µl (group gB+ER804057).

Composition No. 6 contained 2 µg of gBdTM, 1.25 mg of squalene, 0.145 mg of Montane™ VG 85, 0.147 mg of Tween™80 and 1 µg of ER804057 in citrate buffer at pH 6 in 50 µl (group gB+O/W emulsion+ER804057). This composition was obtained by mixing, volume for volume, a solution of gB with an O/W emulsion of the prior art obtained by microfluidization, to which ER804057 was added.

Composition No. 7 contained 2 µg of gBdTM, 1 µg of ER804057 and 60 µg of aluminum hydroxide in a phosphate buffer in 50 µl (group gB+Al+ER804057).

Composition No. 8 contained 2 µg of gB, 1.25 mg of squalene, 0.189 mg of Dehymuls™ SMO, 0.240 mg of Eumulgin™ B1, 0.211 mg of mannitol and 1 µg of ER804057 in PBS buffer at pH 7.4 in 50 µl. This composition was obtained by mixing, volume for volume, a solution of gB with a thermoreversible O/W emulsion PIT-ER804057 at 5% of squalene, obtained by dilution of the stock emulsion of example 1 (group gB+PIT/ER804057).

Eight groups of ten 8-week-old female outbred OF1 mice were immunized subcutaneously, on days D0 and D21, with the compositions indicated above (each group of mice was given 2 injections of the same composition).

Blood samples were taken from the retro-orbital sinus on D20 and on D34 and were used to determine the gBdTM-specific IgG1 and IgG2a antibody concentrations. These assays were carried out by ELISA, by coating the wells of Dynex 96-well microplates with 100 ng (100 µl) of gBdTM in 0.05 M carbonate buffer solution at pH 9.6, at +4° C. overnight.

To determine the neutralizing antibodies, the protocol described by Gonezol E. et al. in J. Virological Methods, 14: 37-41 (1986) was used.

MRC5 cells cultured in an MEM medium containing 10% fetal calf serum were used, between passages 28 and 38, for the microneutralization analyses. The Towne CMV strain (Wistar Institute, Philadelphia, US) purified and propagated on MRC5 cells, having a titer of approximately $2 \times 10^6$ PFU/ml was used as infection strain. A source of complement obtained from the sera of mice from the Virion Ltd Institute (Switzerland) was also used. A mixture of human sera having a titer at 1:128 was used as a positive control, and was included in each microneutralization assay.

The sera to be tested were inactivated by heating at 56° C. for 30 minutes, 105 µl of culture medium (MEM+10% fetal calf serum) were added to a 15 µl aliquot of each inactivated serum, in flat-bottomed 96-well culture plates (⅛ dilution). Serial 2-fold dilutions were then prepared. The control sera were tested in the same way 60 µl of virus suspension containing 3000 PFU and 5 µl of mouse complement were added to each well. After incubation for 1 hour at 37° C. under $CO_2$, $3-4 \times 10^4$ MRC5 cells in a volume of 150 µl of culture medium were added each of the wells. The microcultures were cultured for 4 days. The cytopathic activity of the virus is 100% in the wells which did not contain any sera. On the other hand, an inhibition of the cytopathic activity of the virus was observed in the wells which contained neutralizing sera. The neutralizing antibody titer of a serum corresponded to the inverse of the dilution thereof which inhibited the cytopathic activity of the virus by more than 90%.

The results that were obtained for each group of mice are given in the tables hereinafter:

| Group of mice | IgG1 at D20 | IgG2a at D20 | IgG1 at D34 | IgG2a at D34 | ratio at D34 IgG1/IgG2a |
|---|---|---|---|---|---|
| Group gB | 2.47* | 2.09 | 3.80 | 2.94 | 137 |
| Group gB + O/W emulsion | 4.06 | 2.98 | 5.49 | 4.18 | 143 |
| Group gB + AL | 3.06 | 1.85 | 4.90 | 3.33 | 357 |

-continued

| Group of mice | IgG1 at D20 | IgG2a at D20 | IgG1 at D34 | IgG2a at D34 | ratio at D34 IgG1/IgG2a |
|---|---|---|---|---|---|
| Group gB + PIT | 4.61 | 3.91 | 5.61 | 4.85 | 14 |
| Group gB + ER804057 | 3.09 | 3.12 | 4.43 | 4.16 | 6 |
| Group gB + PIT/ER804057 | 4.78 | 4.58 | 5.83 | 5.74 | 3 |

*mean titer of the dilutions of sera (expressed as $\log_{10}$)

These results show that the PIT/ER804057 emulsion has a greater immunostimulating capacity than the other adjuvants since the specific IgG1 and IgG2a titers obtained in the "gB+PIT/ER804057" group of mice are significantly higher than those obtained in the "gB+AL" or "gB+O/W emulsion" groups of mice. The immunostimulating capacity of the emulsion according to the invention is not due only to the thermoreversible emulsion (PIT emulsion) or to the TLA4 agonist, but to the combination of the two products. The specific IgG1 and IgG2a titers observed in the "gB+PIT" and "gB+ER804057" groups are in fact significantly lower than those which are observed in the "gB+PIT/ER804057" group.

Summarizing table of neutralizing antibody production

| Group of mice | Mean neutralizing antibody titer |
|---|---|
| Group gB | 16** |
| Group gB + O/W emulsion | 32 |
| Group gB + AL | 32 |
| Group gB + PIT | 48 |
| Group gB + ER804057 | 16 |
| Group gB + O/W emulsion + ER804057 | 32 |
| Group gB + AL + ER804057 | 32 |
| Group gB + PIT/ER804057 | 128 |

**inverse of the mean of the serum dilutions which inhibit the cytopathic effect of the virus by more than 90%.

These results show that the immunostimulating composition resulting from the mixing of a CMV envelope antigen with a thermoreversible O/W emulsion containing a TLR4 agonist as described in the invention is that which induces the highest neutralizing antibody titer in the mice. The PIT/ER804057 emulsion has a greater capacity for stimulating the production of neutralizing antibodies than the other adjuvant compositions tested. The PIT/ER804057 emulsion is found to be more effective (in terms of its capacity for stimulating neutralizing antibody production) than a squalene-based O/W emulsion of the prior art containing the same components as the MF59 emulsion, considered up until now to be the reference adjuvant for adjuventing CMV proteins. It is also noted that the addition of a TLR4 agonist to the O/W emulsion of the prior art does not increase the effectiveness off this emulsion (the neutralizing antibody titer remains the same), whereas the effectiveness of a thermoreversible emulsion (PIT) increases when it contains a TLR4 agonist (the neutralizing antibody titer increases).

EXAMPLE IV

Vaccine Composition Against Flu Prepared from an O/W Emulsion According to the Invention Immunostimulating compositions were prepared from an anti-flu vaccine composition comprising the 3 vaccine strains of the 2004 campaign (the A/New Caledonia (H1N1)

strain, the A/Wyoming (H3N2) strain, and the B/Jiangsu strain), which was formulated with various compositions of O/W emulsions or with a suspension of aluminum hydroxide.

Composition No. 1 contained 0.3 µg of hemagglutinin (HA) of each of the viral strains in PBS buffer in 30 µl (0.3 µg HA group).

Composition No. 2 contained 6.3 µg of hemagglutinin (HA) of each of the viral strains in PBS in 30 µl (6.3 µg HA group).

Composition No. 3 contained 0.3 µg of hemagglutinin (HA) of each of the viral strains, 0.65 mg of squalene, 0.075 mg of sorbitan trioleate (Span™ 85) and 0.075 mg of Tween™80 in PBS buffer in 30 µl (0.3 µg HA+O/W emulsion group). This composition was obtained by mixing the anti-flu vaccine composition with an O/W emulsion of the prior art obtained by microfluidization.

Composition No. 4 contained 0.3 µg of hemagglutinin (HA) of each of the viral strains, 0.75 mg of squalene, 0.11 mg of Dehymuls™ SMO, 0.143 mg of Eumulgin™ B1 and 0.138 mg of mannitol and 0.6 µg of ER804057 in PBS buffer at pH 7.4 in 30 µl (0.3 µg HA+PIT/ER804057 group). This composition was obtained by mixing the anti-flu vaccine composition with the thermoreversible emulsion as described in example I and which was diluted beforehand in PBS buffer.

Four groups of eight 8-week-old female BALB/c mice were immunized by administering intradermally (inner face of the ear), on D0, a dose of 30 µl of one of the immunostimulating compositions indicated above.

Blood samples were taken from the retro-orbital sinus on D21 and were used to determine the titers of neutralizing antibodies specific for each viral strain (inhibiting-hemagglutination antibodies (IHA)) obtained in each group of immunized mice. The principle of this assay is based on the ability of flu viruses to agglutinate red blood cells, whereas a serum which contains neutralizing antibodies directed specifically against the HA of the virus inhibits the "hemagglutinating" activity of the virus. Firstly, the nonspecific inhibitors contained in the serum were eliminated by treating the latter with an RDE enzyme (receptor destroying enzyme) provided by Sigma and then bringing them into contact with a 10% solution of chicken red blood cells. A supernatant free of nonspecific inhibitors and which corresponded to a serum diluted to ¹/₁₀th was obtained. Serial 2-fold dilutions of the supernatant in phosphate buffer were subsequently prepared and then 50 µl of each of the dilutions were deposited into the wells of a V-bottomed microplate. 50 µl of a viral suspension originating from a clarified allantoic fluid titered at 4 hemagglutinating units (4HAU) were added to each well. The plate was incubated for 1 hour at laboratory temperature before the addition of 50 µl of a solution of chicken or turkey red blood cells to each of the wells. The plate was left to stand for 1 hour at +4° C. before the assay was read. The presence of hemagglutination inhibition was reflected by the presence of a red spot at the bottom of the microwell, whereas the presence of hemagglutination was reflected by the presence of a pinkish halo in the microwell. The IHA titer was represented by the inverse of the final dilution at which no hemagglutination was observed in the microwell.

The results that were obtained are given in the table below:

| Group of mice | IHA against A/New Caledonia (H1N1) | IHA against A/Wyoming (H3N2) | IHA against B/Jiangsu |
|---|---|---|---|
| 0.3 µg HA | 26*** | 174 | 8 |
| 6.3 µg HA | 247 | 907 | 73 |
| 0.3 µg HA + O/W emulsion | 135 | 987 | 57 |
| 0.3 µg HA + PIT/ER804057 | 290 | 1522 | 98 |

***mean of the IHA titers obtained from the 8 sera of each group of mice.

These results show that the vaccine composition obtained by mixing a flu vaccine with a thermoreversible O/W emulsion containing a TLR4 agonist is that which induces the highest neutralizing antibody titer in the mouse irrespective of the vaccine strain tested, compared with the other vaccine compositions. The PIT-ER804057 emulsion is found to be even slightly more effective (in terms of its capacity for stimulating neutralizing antibody production) than an O/W emulsion of the prior art, the composition of which is similar to MF59. The advantage of this emulsion also lies in the fact that the amount of antigen can be greatly reduced since the results obtained with a dose of 0.3 µg of hemagglutinin mixed with a PIT-ER804057 emulsion are better than those which are obtained with a dose of hemagglutinin that is 20 times higher.

In another assay, the evolution of the IHA titer over time was followed in groups of mice immunized with various immunostimulating compositions prepared from the same vaccine from the 2004 campaign.

Composition No. 1 contained 0.3 µg of hemagglutinin (HA) of each of the viral strains in PBS buffer in 30 µl (0.3 µg HA group).

Composition No. 2 contained 6.3 µg of hemagglutinin (HA) of each of the viral strains in PBS buffer in 30 µl (6.3 µg HA group).

Composition No. 3 contained 0.3 µg of hemagglutinin (HA) of each of the viral strains and 0.6 µg of ER804057 in an aqueous buffer in 30 µl (0.3 µg HA+ER804057 group).

Composition No. 4 contained 0.3 µg of hemagglutinin (HA) of each of the viral strains, 0.30 mg of squalene, 0.044 mg of Dehymuls™ SMO, 0.057 mg of Eumulgin™ B1 and 0.055 mg of mannitol in PBS buffer at pH 7.4 in 30 µl (0.3 µg HA+PIT at 1% group).

Composition No. 5 contained 0.3 µg of hemagglutinin (HA) of each of the viral strains, 0.30 mg of squalene, 0.044 mg of Dehymuls™ SMO, 0.057 mg of Eumulgin™ B1, 0.055 mg of mannitol and 0.6 µg of ER804057 in PBS buffer at pH 7.4 in 30 µl (0.3 µg HA+PIT at 1%/ER804057 group).

Five groups of five 8-week-old female BALB/c mice were immunized by administering intradermally (inner face of the ear), on D0, a dose of 30 µl of one of the immunostimulating compositions indicated above.

Blood samples were taken from the retro-orbital sinus on D23, D51 and D79 and were used to determine the titers of neutralizing antibodies specific for the H1N1 strain (IHA) obtained in each group of immunized mice.

The results that were obtained are given in the table below.

| Group of mice | D23 | D51 | D79 |
|---|---|---|---|
| 0.3 µg HA | 35*** | 53 | 80 |
| 6.3 µg HA | 235 | 243 | 279 |
| 0.3 µg HA + ER804057 | 65 | 211 | 243 |
| 0.3 µg HA + PIT at 1% | 226 | 557 | 735 |
| 0.3 µg HA + PIT at 1%/ER804057 | 226 | 970 | 844 |

***mean of the IHA titers obtained on the 5 sera of each group of mice.

The effectiveness of the PIT-ER804057 emulsion in terms of its ability to produce flu virus Inhibiting-hemagglutination antibodies (protective antibodies) is the result of the combined action of the emulsion and of the TLR4 agonist; the PIT emulsion alone or ER804057 alone is less effective.

EXAMPLE V

Vaccine Composition Against Flu Prepared from an O/W Emulsion According to the Invention Tested in a Population of Primed Young Mice and in a Population of Primed Old Mice The effectiveness of the emulsion according to the invention was tested in the context of a flu vaccine which was administered to primed individuals (i.e; individuals who were either previously in contact with flu, or previously vaccinated against flu).

According to Potter et al (Vaccine, 2003, 21:940-945) this assessment can be done in mice, primed with a trivalent flu vaccine given by intramuscular, route.

Five groups of ten 8 to 10-week-old female C57Bl/6 mice were given by IM one dose of a trivalent flu vaccine, which contained 1.5 μg of HA of each of the following strains: A/New Caledonia/20/99 (H1N1), A/New York/55/04 (H3N2) and B/Malaysia/2506/04.

On D28, all groups but "PBS group" that was given a phosphate buffer solution, were given by the intradermic route, 30 μl of different flu vaccine compositions which were prepared from another trivalent flu vaccine (A/New Caledonia/20/99 (H1N1), A/Wellington/01/04 (H3N2) and B/Jiangsu/10/03) which was different from that was used for priming.

One group was given a composition containing 0.3 μg HA of each of the strains in phosphate buffer (0.3 μg HA group).

One group was given a composition containing 6.3 μg HA of each of the strains in phosphate buffer (6.3 μg HA group).

One group was given a composition containing 0.3 μg HA of each of the strains, 0.3 mg of squalene, 0.44 mg of Dehymuls™ SMO, 0.057 mg of Eumulgin™ B1, and 0.055 mg of mannitol in a phosphate buffer (PBS) This composition that contained 1% of squalene (w/w) was obtained by mixing the flu vaccine with an O/W emulsion obtained by diluting a thermoreversible O/W prepared as described in example 1, except for the fact that the aqueous phase does not contain any ER 804057 (0.3 μg HA+PIT 1% group).

One group was given a composition containing 0.3 μg HA of each of the strains, 0.3 mg of squalene, 0.44 mg of Dehymuls™ SMO, 0.057 mg of Eumulgin™ B1, 0.055 mg of mannitol, 0.6 μg ER 804057 in a phosphate buffer (PBS). This composition that contained 1% of squalene (w/w) was obtained by mixing the flu vaccine with an O/W emulsion obtained by diluting a thermoreversible O/W prepared as described in example 1 (0.3 μg HA+PIT 1%/ER 804057 group).

Blood samples were taken on D50 to determine the titers of neutralizing antibodies (IHA) specific for each strain.

The results that were obtained are given in the table below

| Group of mice | IHA against A/New Caledonia (H1N1) | IHA against A/Wellington (H3N2) | IHA against B/Jiangsu |
|---|---|---|---|
| PBS | 52* | 48 | 13 |
| 0.3 μg HA | 95 | 226 | 57 |
| 6.3 μg HA | 190 | 640 | 226 |
| 0.3 μg HA + PIT1% | 431 | 640 | 290 |
| 0.3 μg HA + PIT1%/ER804057 | 698 | 2348 | 640 |

*:mean of the IHA titers obtained from the 10 sera of each group of mice

These results shows that the mean IHA titer in the group of primed mice immunized with a vaccine composition (0.3 μgHA+PIT1%/ER 804057) containing a low concentration of squalene (1%) and a low amount of TLR4 agonist (0.6 μg of ER804057) is significantly higher than the mean IHA titers obtained in the groups of mice immunized with a trivalent flu vaccine with the same dose of HA (0.3 μg HA group) but without adjuvant, or immunized with a trivalent flu with a dose of HA that is 20 times higher (6.3 μg HA group). These results show that it is advantageous of using the emulsion PIT 1%/ER 804057 which was prepared by dilution of a thermoreversible O/W emulsion as described in example 1, even in a population of individuals already primed against flu, since the amount of HA antigen can be greatly reduced without affecting the IHA titers. Moreover, the "boosting effect on the IHA titers" is very strong The same immunization schedule was applied to 17 month old male C57BL6 mice as previously recorded IHA titers against A/Wellington (H3N2) were measured in mice that were immunized either with 6.3 μg of hemagglutinin of each of the viral strains, either with 0.3 μg of hemagglutinin of each of the viral strains in PIT emulsion at 1%, or with 0.3 μg of hemagglutinin of each of the viral strains in PIT emulsion at 1% with ER804057. The results that were obtained are given in the table below.

| Group of mice | IHA against A/Welliington (H3N2) |
|---|---|
| 6.3 μg HA | 104* |
| 0.3 μg HA + PIT at 1% | 247 |
| 0.3 μg HA + PIT at 1%/ER804057 | 476 |

*mean of the IHA liters obtained from the 10 sera of each group of mice

These results show the advantage of using the emulsion PIT 1%/ER 804057 which was prepared by dilution of a thermoreversible O/W emulsion as described in example 1, in a aged population already primed against flu since the amount of HA antigen can be greatly reduced without affecting the IHA titers.

What is claimed is:

1. An Oil-in-Water (O/W) emulsion comprising, i) a TLR4 agonist, called TLR4, the chemical structure of which does not comprise a sugar ring, ii) squalene, iii) an aqueous solvent, iv) a nonionic hydrophilic surfactant which is a polyoxyethylene alkyl ether, and v) a nonionic hydrophobic surfactant, in which the TLR4 agonist is the chemical compound ER804057, the nonionic hydrophilic surfactant is ceteareth-12, the nonionic hydrophobic surfactant is sorbitan monooleate and the aqueous solvent is a phosphate buffer or a citrate buffer, and wherein the emulsion is thermoreversible.

2. The emulsion as claimed in claim 1, in which:
a) the amount of squalene in the emulsion is between 5% and 45% of the total weight of the emulsion,
b) the ratio of the amount of squalene to the total amount of ceteareth-12 and of sorbitan monooleate is between 2.0 and 4.0,
c) the amounts of ceteareth-12 and of sorbitan monooleate are such that the HLB is between 8.5 and 10, and
d) the ratio of the amount of ER 804057 to the total amount of ceteareth-12 and of sorbitan monooleate is between $0.01 \times 10^{-2}$ and $2 \times 10^{-2}$.

3. The emulsion as claimed in claim 2, further comprising mannitol in which the amount is between 0.1 and 10% of the total weight of the emulsion.

* * * * *